United States Patent [19]

Francois

[11] Patent Number: 4,784,607
[45] Date of Patent: Nov. 15, 1988

[54] DENTAL IMPRESSION SYRINGE

[75] Inventor: Michel Francois, Saint Ismier, France

[73] Assignee: Stabyl (s.a.r.l.) Chemin des Clos, France

[21] Appl. No.: 934,849

[22] Filed: Nov. 25, 1986

[30] Foreign Application Priority Data

Nov. 25, 1985 [FR] France .................. 85 17550

[51] Int. Cl.⁴ .............................................. A61C 5/04
[52] U.S. Cl. ........................................ 433/90; 433/89
[58] Field of Search ............................ 433/80, 89, 90;
604/218

[56] References Cited

U.S. PATENT DOCUMENTS 723,822  3/1903  Buchanan .............................. 433/90
2,825,134 3/1958  Hicks .................................... 433/90
3,346,147 10/1967 Higgins et al. ....................... 433/90

FOREIGN PATENT DOCUMENTS 675455  1/1942  Fed. Rep. of Germany ........ 433/90
549938 12/1942  United Kingdom ................. 433/90

Primary Examiner—John J. Wilson
Attorney, Agent, or Firm—Lowe, Price, LeBlanc, Becker & Shur

[57] ABSTRACT

A syringe for injecting a pasty material comprising: a main cylindrical body; a piston slidable in the body; and a tube slotted in the largest part of its length and provided with a handling ring at its rear part, the internal diameter of the main cylindrical body substantially corresponding to the external diameter of the tube so that, when the tube is arranged into the cylinder, this set defines an injection chamber delimited by the internal wall of the tube and, in front of the slot of the tube, by the internal wall of the cylindrical body.

8 Claims, 3 Drawing Sheets

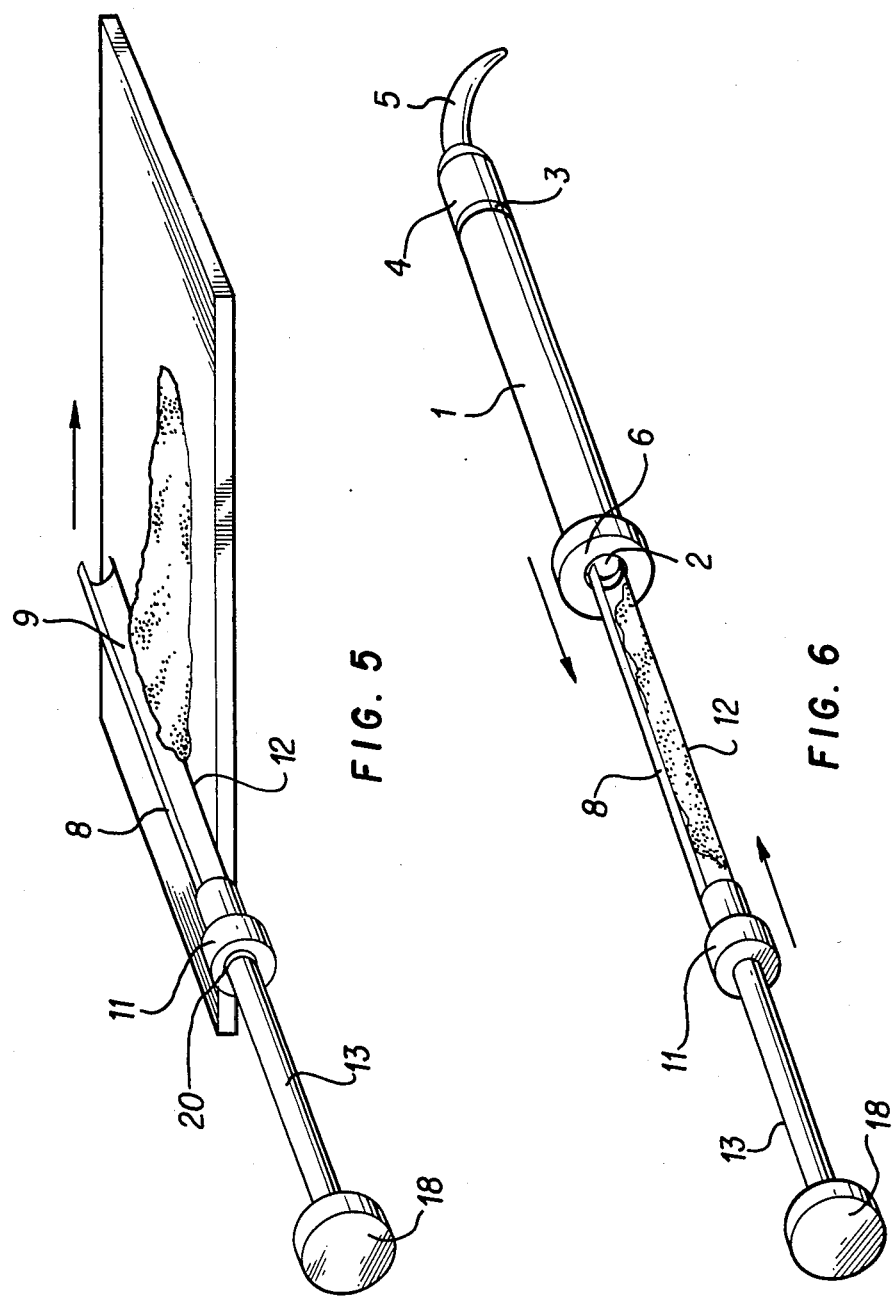

DENTAL IMPRESSION SYRINGE

TECHNICAL FIELD

The invention relates to a syringe with an incorporated filling system for injecting pasty materials for taking dental impressions.

BACKGROUND OF THE INVENTION

Dental surgeons currently use for taking impressions various types of materials. All those materials, at the moment of the injection have a pasty consistency. Example of such materials are:

the alginates, comprising powder alguae that the user mixes before using in a bowl with water for obtaining a pasty material that gels after some minutes;

the silicones, thiokols or elastomers which are viscous pastes that are mixed, before using, on a mixing plate or block with a catalysing or hardening paste or liquid. Those materials are polymerising after some 20 minutes.

A problem with all those materials is the relatively short time—generally within 2 to 4 minutes—that is available for the user between the moment at which he starts the mixing and the moment where the material begins its polymerisation or gelification and is no longer injectable.

The prior art syringes for injecting those pasty impression materials are difficult to fill because the diameter of their internal bore is small.

A plurality of methods are used for filling classical syringes. First, generally, the syringes are filled by scraping their rear part on the mixture bowl for entering the material by gravitation. By this method, no suitable filling is obtained because it necessarily causes a mixture of air and material to enter the syringe, causing, during the injection, air bubbles to appear whereby impression quality is poor. Additionally, it is very difficult, within a short time duration, to scrape onto the whole surface of the mixing block the totality of the mixture, a part of the material is lost.

Syringes with charging systems integral with, or added to and taken away, their rear part are also known, those charging systems being filled with a spatula for taking the material from the mixing block or bowl. Those methods are not satisfactory because they cause time losses due to the handling of filling spare parts such as the piston of integral chargers or removable charger-piston sets. Those methods also cause a material loss and are often complicated to use and dirty the syringes.

Systems with double cylinder and double piston syringes are also known and can even be used for mixing some very fluid impression material. Those systems are not usable for pasty materials and are generally cumbersome and not suitable for injecting small quantities of materials.

It appears that those prior systems do not simultaneously present the following qualities: quickness of use, efficiency, material savings, cleanliness, and simplicity of use.

SUMMARY OF THE INVENTION

It is an object of the invention to provide for a new syringe presenting simultaneously all those advantageous features.

For attaining those objects, the invention provide for a syringe for injecting a pasty material comprising a main cylindrical body; a piston slidable in said body; a tube slotted in the largest part of its length and provided with a handling ring at its rear part, the internal diameter of the main cylindrical body substantially corresponding to the external diameter of the tube so that, when the tube is arranged into the cylinder, this set defines an injection chamber delimited by the internal wall of the tube and, in front of the slot of the tube by the internal wall of the cylinder.

BRIEF DESCRIPTION OF THE DRAWINGS

Those objects, features and advantages and others of the invention shall be disclosed in greater detail in the following description of a preferred embodiment made in connection with the attached drawings wherein:

FIGS. 5, 6 and 7 illustrate the utilization of a syringe according to the invention.

DESCRIPTION OF THE INVENTION

Figure 1:
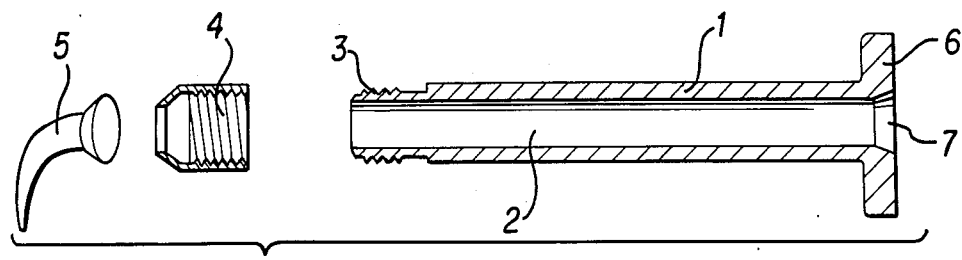
FIG. 1 is a cross-section exploded view of the main body of the syringe, its injection tip and a fixing nut.

FIG. 1 shows the main body 1 of the syringe comprising a tube, for example of a plastic material, with an internal bore 2; the body comprises on its front side an external threading 3 for receiving a nut 4 blocking an injection tip 5. The rear side comprises a flange 6 for allowing the user to maintain the syringe body 1 between his fingers. The rear aperture of the syringe is bevelled as shown by reference numeral 7 for facilitating the penetration of the sampling tube according to the invention.

Figure 2:
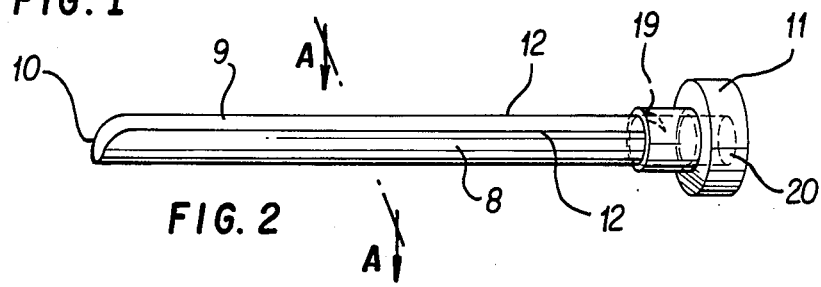
FIG. 2 shows a sampling tube according to the invention.

FIG. 2 shows a sampling tube 8 according to the invention having an external diameter equal to the internal diameter of the bore 2 of the body 1. This tube is slotted along its length. The width of the slot is comprised between one quarter and one half of the diameter of the tube 8. The slot extends for example on the whole length of the tube or only on a major part thereof. The extremity 10 of the tube is bevelled or rounded in order to facilitate the introduction of the tube into the body through the bevelled aperture 7. A ring 11 surrounds the rear part of the tube for facilitating its handling. The slot 9 can extend also through this ring. The slot 9 is defined by two lines 12 which are sharpened for facilitating the scraping of the impression material during the sampling. The tube 8 is conveniently made of a metal and preferentially stainless steel.

Figure 3:
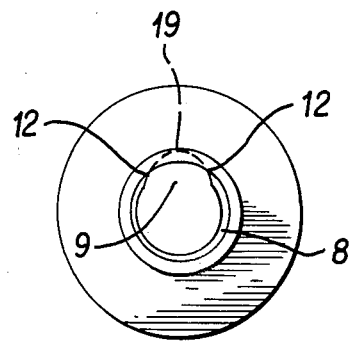
FIG. 3 is an enlarged cross-section view according to line A—A of FIG. 2.

As shown also in the cross-section view of FIG. 3, the front aperture of the handling ring 11 is provided with a bevel 11. The rear part of the handling ring 11 and accordingly of the sampling tube 8 is also provided with a bevel 20.

Figure 4:
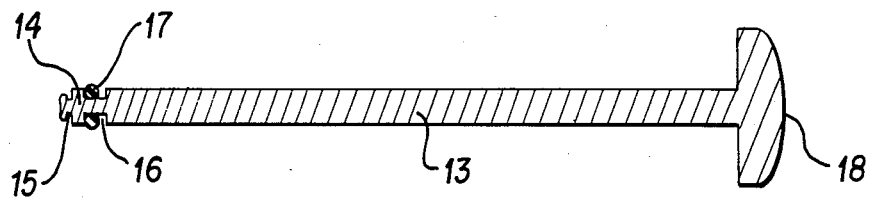
FIG. 4 is a cross-section view of the injection piston.

FIG. 4 shows a piston 13 comprising at its front part 14 a first annular groove 15 and a second annular groove 16, said second annular groove 16 receiving an O-ring 17. The groove 16 is wider than the cross-section of the O-ring 17 and has a diameter smaller than the internal diameter of the O-ring 17. At its rear part, the piston 13 comprises a pushing button 18. The piston 13 can be made of plastics.

Some successive steps of using a syringe according to the invention will be explained in connection with FIGS. 5 to 7.

Before making any operation, on the one hand the user fixes by means of the nut 4 the injection tip 5 onto the threading 3 of the main body 1. On the other hand, he arranges the piston 13 in the sampling tube 8 by entering its front portion 14 into the bevelled aperture 20 of the tube, the O-ring 17 not being engaged further than the end of the bevel 19. Then those two sets are let apart and the pasty material mixture is prepared.

Once the mixture is made, the user takes, by means of the handling ring 11, the set tube-piston. He arranges the slot 9 in front of the material to be sampled, one of the lines 12 being in contact with the mixing block or a wall of the mixing bowl which, as well known by surgeon-dentists, is elastic and has one vertical wall.

As shown in FIG. 5, the user moves the set tube-piston in the direction of the arrow while maintaining the line 12 in contact with the surface of the mixing plate, block or bowl and therefore fills the sampling tube 8 through the slot 9.

After sampling, as shown in FIG. 6, the user, handling the ring 11, presents the bevelled or rounded extremity 10 of the tube towards the bevelled back aperture 7 of the main body and pushes the sampling tube 8 inside the bore 2 of the main body 1.

Figure 7:
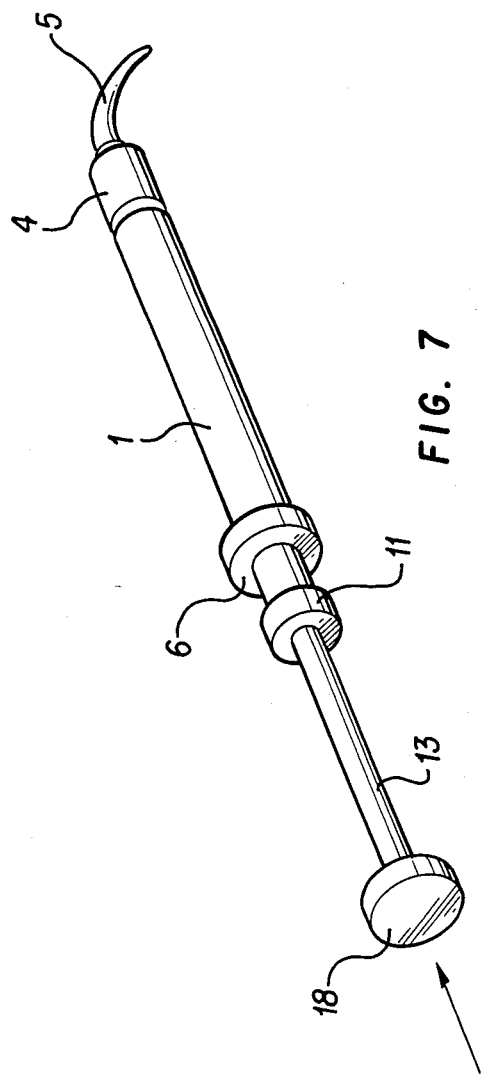

Then, as shown in FIG. 7, the user can inject the pasty material by pushing onto the button 18 for penetrating the piston 13 into the cavity partially delimited by the internal surface of the tube 9 and partially delimited by the bore of the main body in front of the slot. The operation is then identical to the one of any syringe.

Once the injection achieved, the user waits for the full polymerisation or gelification of the material prior to cleaning its syringe. He has then to take off the piston 13 while slightly rotating same. The O-ring 17 is extracted without problem through the internal bore of the ring 11 due to the bevel 19. The gelified or polymerised material which remained in the injection tip 5 sticks to the extremity 14 of the piston 13 due to the presence of the first groove 15. Then, the sampling tube 8 can be taken out of the main body 1 and easily cleaned by means of an elongated brush.

It therefore appears that the syringe according to the invention attains all the objects of simplicity, rapidity, cleanliness, and efficiency of the invention.

I claim:

1. A syringe for injecting a pasty material comprising: a main body formed with a longitudinal passage; and a tube removably mounted within the passage to extend through the body, a piston mounted to extend slidably through the tube, said tube formed with a longitudinal slot in a side wall thereof and provided with a handling ring at a rear part of the tube, the cross section of the passage of the main body substantially corresponding to the cross section of the tube such that the tube inserted to extend within the body establishes an injection chamber defined by an internal wall of the tube and an internal wall passage of the body extending coextensive with said slot, said slot being defined between a pair of longitudinal generally sharp edges formed in the tube side wall, each edge extending between the internal wall and an external wall of the tube to directly connect said walls together along the edge so that each edge functions as a scraping edge enabling it to move along and in contact with a surface of a mixing plate on which pasty material is disposed to enable said material to be scraped by the edge directly onto the internal wall of the tube prior to inserting the tube into the body.

2. The syringe of claim 1, wherein the width of the slot is approximately between one quarter and one half of the periphery of the tube.

3. The syringe of claim 1, wherein the slotted portion of the tube crosses the handling ring, the slot extending on the whole length of the tube.

4. The syringe of claim 1, wherein the ring is bevelled on its front side.

5. The syringe of claim 1, wherein the front extremity of the sampling tube is bevelled or rounded.

6. The syringe of claim 1, wherein the rear aperture of the handling ring is bevelled.

7. The syringe of claim 1, wherein the piston comprises proximate its tip a first groove and a second groove for receiving an O-ring.

8. The syringe of claim 1, wherein the injection piston comprises, close to its tip a groove for receiving an O-ring, said groove being wider than the cross-section of the OR-ring and having a diameter smaller than the internal diameter of said O-ring.

* * * * *